(12) United States Patent
Eschler et al.

(10) Patent No.: US 9,028,431 B2
(45) Date of Patent: May 12, 2015

(54) STATUS DETECTING DEVICE TO BE ATTACHED TO A LIVING BEING

(75) Inventors: Johannes Eschler, Ditzingen (DE); Hans-Peter Klose, Stuttgart (DE); Anke Jedrkowiak, Markgroeningen (DE)

(73) Assignee: Robert Bosch GmbH, Stuttgart (DE)

( * ) Notice: Subject to any disclaimer, the term of this patent is extended or adjusted under 35 U.S.C. 154(b) by 267 days.

(21) Appl. No.: 13/256,000

(22) PCT Filed: Jan. 18, 2010

(86) PCT No.: PCT/EP2010/050489
§ 371 (c)(1),
(2), (4) Date: Nov. 18, 2011

(87) PCT Pub. No.: WO2010/105860
PCT Pub. Date: Sep. 23, 2010

(65) Prior Publication Data
US 2012/0059284 A1 Mar. 8, 2012

(30) Foreign Application Priority Data

Mar. 16, 2009 (DE) .......................... 10 2009 001 565

(51) Int. Cl.
| G08B 23/00 | (2006.01) |
| A61B 5/117 | (2006.01) |
| A61B 5/103 | (2006.01) |
| G01C 5/06 | (2006.01) |
| A61B 5/11 | (2006.01) |
| A61B 5/00 | (2006.01) |
| G08B 21/04 | (2006.01) |

(52) U.S. Cl.
CPC ................ *G01C 5/06* (2013.01); *A61B 5/1117* (2013.01); *A61B 5/6831* (2013.01); *A61B 2560/0242* (2013.01); *A61B 2562/0219* (2013.01); *G08B 21/043* (2013.01); *G08B 21/0446* (2013.01)

(58) Field of Classification Search
USPC ............... 600/595; 340/573.7, 573.1; 379/45; 455/404, 456, 419
See application file for complete search history.

(56) References Cited

U.S. PATENT DOCUMENTS

| 2002/0193091 A1* | 12/2002 | Zmarthie ....................... 455/404 |
| 2007/0218823 A1 | 9/2007 | Wolf |
| 2008/0129518 A1* | 6/2008 | Carlton-Foss ............. 340/573.1 |
| 2009/0322540 A1* | 12/2009 | Richardson et al. ........ 340/573.7 |

FOREIGN PATENT DOCUMENTS

| JP | 2004 096457 | 3/2004 |
| JP | 2005 230340 | 9/2005 |
| WO | 98/58236 | 12/1998 |

* cited by examiner

*Primary Examiner* — Brian Szmal
(74) *Attorney, Agent, or Firm* — Kenyon & Kenyon LLP

(57) ABSTRACT

A status detecting device is described for being attached to a living being, in particular a person, to detect the position of the body of the living being, having a first sensor, configured as an acceleration sensor and/or a gyroscopic sensor. An additional, second sensor, configured as a height measuring sensor, is also provided. Also described is a corresponding method.

17 Claims, 2 Drawing Sheets

STATUS DETECTING DEVICE TO BE ATTACHED TO A LIVING BEING

FIELD OF THE INVENTION

The present invention relates to a status detecting device to be attached to a living being, in particular to a person, to detect the position of the body of the living being. A corresponding method is also described.

BACKGROUND INFORMATION

Detecting the movement of living beings, in particular of persons, has become increasingly important over the years in sports, wellness, and fitness and also in particular in medicine, for example, in diagnosis, treatment and rehabilitation. For example, there are systems which are known in the fields of sports and fitness, in which the movement times and step numbers or step sequences are measured, as discussed in WO 1998058236, for example. In the medical field in particular, parameters pertaining to gait such as stepping times, right-left gait symmetry and force of tread are of interest here, movement monitors using software being available today, making it possible to ascertain such parameters. To do so, the acceleration values of the body in the longitudinal, transverse and/or vertical directions are detected by acceleration sensors attached to the body. Such signals are typically evaluated using step counting algorithms. For special medical research, in particular in gerontology or in therapeutic management of chronic diseases, a differentiated classification of movements detected according to "walking," "sitting," "standing" and "lying" is desirable, and such a classification should be possible in an everyday environment without any major equipment complexity in order not to restrict the affected persons due to an apparatus to be carried along and multiplex cabling.

Since the corresponding group of people should carry such devices on them at all times, if possible, but at the same time their mobility and motor system are often restricted, the systems known from the related art are not suitable. The data ascertained using detection devices known from the related art additionally do not generally enable a reliable differentiation between the states "sitting" and "standing" or a reliable detection of a transition from sitting to standing or vice versa. Japanese patent document JP-2004096457 also discusses a monitoring device for clinic beds, monitoring a patient lying in a clinic bed with the aid of a three-dimensional sensor. One disadvantage of this is that this system has only a very limited area of use.

SUMMARY OF THE INVENTION

In a very advantageous manner, the restrictions known from the related art are eliminated by the status detecting device proposed according to the present invention, enabling universal use in the fields of sports, fitness/wellness and medicine or treatment and rehabilitation. To do so, a status detecting device to be attached to a living being, in particular to a person, is proposed in order to detect the position of the body of the living being, having a first sensor which is designed as an acceleration sensor and/or as a gyroscopic sensor. An additional second sensor is provided here, this one being designed as a height measuring sensor. With the help of the height measuring sensor, it is possible to verify changes in the position of the body detected by the first sensor. For example, the transition from sitting to standing, which was detected by the first sensor as described, may be verified with the aid of the height measuring sensor, so that a height difference in the length of the thigh, for example, is detected when standing up. It is in principle also possible to ascertain such transitions from sitting to standing or vice versa from pure acceleration values such as those detected by the first sensor. However, there is increased uncertainty here regarding whether such a change in position has actually occurred. For strict verification of such a change in position, a simple and inexpensive monolithic height meter may be used, for example, to verify the change in position of the body.

In another specific embodiment, it is provided that the height measuring sensor is an air pressure detecting sensor. Air pressure detecting sensors are known as height measuring sensors in the related art. A height is ascertained here indirectly via a change in the prevailing air pressure. Micromechanically produced very accurate height measuring sensors/air pressure detection sensors may be used here to be able to reliably detect even minor differences in air pressure such as those which correspond, for example, to changes in the height position in the area of a human thigh length.

In another specific embodiment, a compensation device of the air pressure detecting sensor is provided to compensate for fluctuations in air pressure not due to changes in position. In the indirect method of ascertaining the height or changes in height in the position via the air pressure, sources of error may occur, caused by such fluctuations in air pressure which cannot be attributed to a change in position but instead must be attributed to other influences in the surroundings, for example, opening of windows or doors in air-conditioned rooms, usually resulting in a change in the ambient pressure within a very short period of time. Such fluctuations in air pressure are detected by the compensation device and are compensated with regard to detection of a change in position. This prevents a faulty assumption of a change in position.

A specific embodiment includes a plausibility check unit, which compares a change in the position of the body of the living being which is detected by the first sensor with data coming from the height measuring sensor. An adjustment is made here between data supplied by the first sensor, which is designed as described above as an acceleration sensor and/or as a gyroscopic sensor, with data supplied by the height measuring sensor. The comparison of data from the first and second sensors allows reliable information to be obtained about the change in position of the body. In other words, a change in position as detected by the first sensor is compared with data acquired by the second sensor or vice versa, so that a change in position is actually assumed only when the data of both sensors show such a change in position. At the same time, an accurate quantification of the change in position is possible in this way.

The status detecting device may be configured as a modular unit. This means that the first and second (both) sensors are combined in a single modular unit, which may be with additional devices, for example, the plausibility device and the compensation device, so that this one modular unit alone assumes all the functions of the status detecting device, in particular including storage and/or evaluation and/or providing interfaces and/or signaling (warning tones, warning displays). In this way, for example, as a modular unit attached to the body of the living being above the hip, a comfortable design, which is not restrictive and/or hindering in everyday use, is made possible. It is readily possible for patients, the injured or the elderly in particular to conveniently wear the status detecting device in an advantageous manner. Due to the very reliable detection of changes in position, in particular changes in height, a warning device may also be implemented very advantageously, for example, detecting when a patient wearing the status detecting device falls, for example, and then calling an emergency physician or an ambulance service via an emergency call system (cell phone, radio), for example. Such a fall detection may take place very advantageously, for example, by comparing the change in position of the body (in particular as a change in height) with a time base, such as that which may be integrated very easily into the status detecting device through digital time measuring devices. In contrast with intentionally standing up or sitting down, a fall occurs with a different movement/time profile, so that it is readily possible to differentiate very reliably between a fall and intentionally sitting down, lying down or standing up based on the period of time ascertained for the change in height. It is particularly possible here to wait, after detecting such a fall, for an acknowledgement from the patient, for example, by pushing a button. If such an acknowledgement does not arrive within a predefinable period of time, an emergency call is triggered because then it must be assumed that the patient is no longer capable of helping himself. However, if the patient sends an acknowledgement after being called by the status detecting device within the specified period of time, no emergency call is triggered because, based on the acknowledgement, it may be assumed that the patient is capable of helping himself. It is possible in this way to provide a false-alarm-proof emergency alarm system in an advantageous manner.

In addition, a method for detecting a position of a body of a living being is proposed, in which an acceleration and/or an angular position of the body is detected by a first sensor attached to the body. It is provided here that the height of the body is determined with the aid of another sensor. In addition to the position data supplied by the first sensor attached to the body with respect to an acceleration and/or an angular position of said body, data of another sensor with respect to a position of the body are determined. Changes in position of the body may consequently be ascertained by comparison of the data of the first sensor with the data of the additional second sensor, then subjected to a plausibility check and verified. Accelerations, angle changes and changes in the height of the body may be used here to yield a movement profile and a movement evaluation in a very advantageous manner.

Additional advantageous specific embodiments are derived from the further descriptions and from combinations thereof.

The exemplary embodiments and/or exemplary methods of the present invention are described in greater detail below on the basis of an exemplary embodiment without being limited to that.

DETAILED DESCRIPTION

Figure 1:
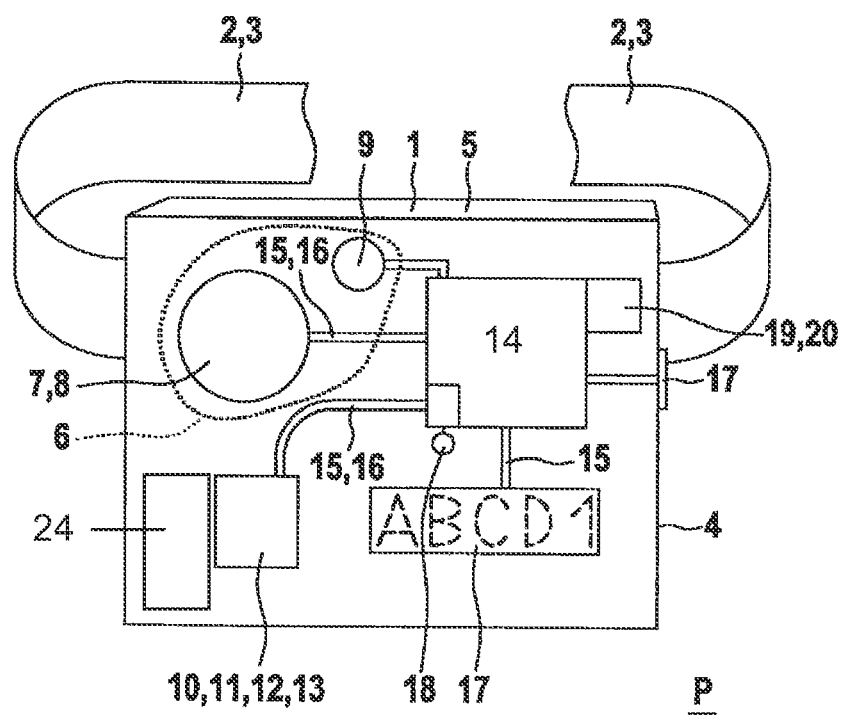
FIG. 1 shows a schematic representation of a status detecting device according to the present invention.

FIG. 1 shows a status detecting device 1 to be attached to a living being (not shown) by attachment arrangement 2, for example, belts 3. Status detecting device 1 is designed as a modular unit 4, which has in a compact housing 5 a first sensor 6, which is formed in the present case by an acceleration sensor 7, namely a multiaxial acceleration sensor 8 and a gyroscopic sensor 9 and another sensor 10, namely a second sensor 11, which is an air pressure detecting sensor 12, which acts as a height measuring sensor 13 by indirect measurement of height based on ambient air pressure P. Acceleration sensor 7 as a multiaxial acceleration sensor 8 detects accelerations acting on it here in its axes (not shown here), in particular in the three geometric axes. Gyroscopic sensor 9 detects changes in angular position caused by movement of modular unit 4 or of the living being (not shown) carrying modular unit 4. Specific embodiments having only acceleration sensor 8 (not including gyroscopic sensor 9) as first sensor 6 are of course also possible.

The data of first sensor 6 are sent to an evaluation unit 14 by suitable electrical connections 15, for example, printed conductors 16, which evaluates the changes in position of modular unit 4 on the basis of the data from first sensor 6, records the information and makes it available via an interface 17 for evaluations performed outside of status detecting device 1, for example, via a computer system (not shown). At the same time, a display 17 for displaying status messages or alarm messages is connected via suitable electrical connections 15. Data coming from first sensor 6 and evaluated as movement data by evaluation unit 14 are not reliable under all circumstances. Second sensor 11 as height measuring sensor 13 therefore supplies additional data, namely height data with regard to the position of status detecting device 1 (of modular unit 4) to evaluation unit 14, which are compared with the data originating from first sensor 6. To increase the reliability of the height data of height measuring sensor 13, evaluating device 14 is provided with a compensation device 18, which signals non-position-dependent fluctuations in ambient air pressure P to evaluation unit 14 and thereby compensates for them (for example, via a pressure profile and/or another air pressure sensor). This prevents a false detection of a change in the height position by air pressure detecting sensor 12 when there are changes in ambient air pressure P.

If an acceleration of modular unit 4 is detected by the first sensor, in particular acceleration sensor 7, this may be interpreted as a change in position in evaluation unit 14. If at the same time no change in height is detected by second sensor 11 (in particular after compensation by compensation unit 18), then a change in height is not to be assumed. If a change in angular position is detected by first sensor 6, in particular by gyroscopic sensor 9, then a change in height is again not to be assumed unless second sensor 11 reports a change in height. This definitely increases the accuracy of the overall system with regard to changes in height as a condition of the body (not shown) to which status detecting device 1 is attached for example, for diagnostic purposes. If height measuring sensor 13 supplies data indicating a change in height to evaluation unit 14, this is attributed to changes in air pressure (possibly also without compensation unit 18) unless at the same time (at least) one change in the angular position is reported to evaluation unit 14 via gyroscopic sensor 9 of first sensor 6 and/or an acceleration is reported via acceleration sensor 7 of first sensor 6. Furthermore, an accurate time detecting device 19, for example, as a digital clock 20, is assigned to evaluation unit 14, allowing statements about the chronological sequence of changes in status/changes in height and angular position and/or acceleration. For example, this makes it readily possible to differentiate a fall from sitting down intentionally because a fall usually takes place within a much shorter time. An alarm unit (not shown here) may, for example, send an alarm/make an emergency call in cases when a fall is detected. This alarm unit may be integrated into the status detecting device, namely modular unit 4.

Figure 2:
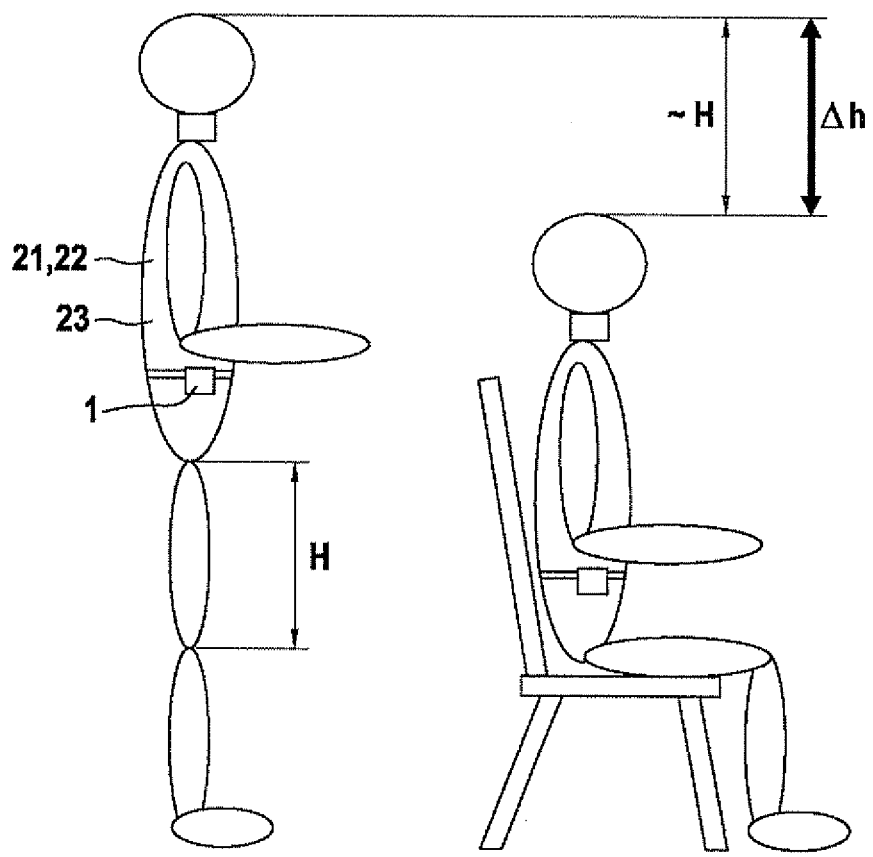
FIG. 2 shows a schematic diagram of the functionality of the status detecting device.

FIG. 2 shows a person 21 as living being 22, carrying status detecting device 1, which is shown schematically here on a belt in a comfortable position and method of attachment.

Person 21 is shown once standing and once in a sitting position, the difference in height Δh corresponding approximately to thigh length H of person 21. The transition between the standing state and the sitting state as the corresponding position of body 23 of person 21 in space is detected by status detecting device 1 via first sensor 6, which is described with regard to FIG. 1 and second sensor 11, where second sensor 11 has the particular task of ascertaining the difference in height Δh. Thigh length H is used for verification of the transition from a sitting position to a standing position or vice versa, this being preselectable via status detecting device 1, for example, in a memory area of evaluation unit 14 of status detecting device 1. These status transitions between sitting and standing positions may be detected very accurately in this way. In standing up, the so-called sitting-standing transfer, second sensor 11 (all the reference numerals not shown in FIG. 2 may be found in FIG. 1) detects a positive difference in height extent Δh corresponding approximately to thigh length H of person 21 wearing corresponding status detecting device 1. Status detecting device 1 is therefore calibratable with corresponding individual thigh length H of corresponding individual person 21; for example, this thigh length H may be programmed into the system or otherwise entered or ascertained on the basis of the difference in height extent Δh thereby ascertained by standing up and sitting down performed one or more times in a calibration mode of status detecting device 1. For such calibrations and other interactions, status detecting device 1 has operating elements (not shown here), for example, pushbuttons. A corresponding negative difference in height extent Δh is ascertained when sitting down from a standing position (the so-called standing/sitting transfer). In addition to this difference in height extent Δh, accelerations are ascertained by acceleration sensor 7 and/or changes in angular position by gyroscopic sensor 9, which may be used for verification and a plausibility check. A plurality of different movement data and/or position data of body 23 of person 21 wearing the status detecting device is detectable with status detecting device 1 proposed here having the features according to the present invention as described here, so that status detecting device 1 may be used universally and may be used in the fields of fitness and wellness in particular as well as in sports in addition to the care of elderly or fragile persons. In a specific embodiment, the status detecting device has memory elements (not shown here) that are suitable for long-term detection and are assigned to evaluation unit 14 and allow online evaluation on the device itself in real time or in response to a query and likewise allow offline evaluation on a computer system (not shown here), so that training results, in particular deviations in the motor system and in movement sequences as well as motor behavior patterns, may be detected and evaluated. Furthermore, very good monitoring of fragile or helpless persons is possible in this way so that falls, for example, may be detected much more reliably than in approaches known from the related art. In the proposed variant in particular, in which an alarm system 24 is assigned to status detecting device 1, for example, via radio or cell phone, or integrated into it, a very high reliability and safety may be achieved for the respective wearer. For example, such a system may also request an acknowledgement of whether the movement in question was intended or not within a predefinable period of time before delivering an alarm. If there is an acknowledgement, then no alarm is issued; if there is no acknowledgement, status detecting device 1 concludes that the wearer has fallen and sends an alarm to the stored targets. Very good monitoring may be achieved with a very good security against false alarms in this way.

What is claimed is:

1. A status detecting device, which is for attaching to a living being, including a person, comprising:
    a detecting arrangement to detect a relative change in position of the body of the living being, wherein the detecting arrangement includes an at least one first sensor and an at least one additional second sensor, which includes a height measuring sensor; and
    an evaluation arrangement to receive, upon detection of the relative change in position of the body of the living being, at least (i) a signal indicating a detected relative change in position and (ii) data from the height measuring sensor, and to perform a plausibility check by comparing the detected relative change in position with the data from the height measuring sensor;
    wherein the relative change in position of the body is detected by the at least one first sensor if the position of the body changes from a first state to a second state.

2. The status detecting device of claim 1, wherein the height measuring sensor includes an air pressure detecting sensor.

3. The status detecting device of claim 1, further comprising:
    a compensation unit of the air pressure detecting sensor for compensation of air pressure fluctuations not due to changes in position.

4. The status detecting device of claim 1, wherein the at least one first sensor includes at least one of an acceleration sensor and a gyroscopic sensor.

5. The status detecting device of claim 1, wherein the alarm system includes at least one warning device for providing a warning when the device detects a fall of the living being wearing the status detecting device by placing a call via an emergency call system.

6. The status detecting device of claim 5, wherein the detecting arrangement of the status detecting device is configured to determine that the fall has occurred by comparing a change in a position of a body of the living being over time to a known movement over time profile.

7. The status detecting device of claim 6, wherein the change in position of the body is a change in height.

8. The status detecting device of claim 6, further comprising:
    at least one integrated digital time measuring device that measure the time.

9. The status detecting device of claim 1, wherein the first state and the second state are selected from a set of states, including a sitting state, a standing state, a lying down state, and a walking state.

10. The status detecting device of claim 1, wherein responsive to the data from the height measuring sensor indicating no relative change in position of the body, the plausibility check indicating that the detected relative change in position was an error, and wherein responsive to the data from the height measuring sensor indicating a relative change in position of the body, the plausibility check confirming that the detected relative change in position was correct.

11. The status detecting device of claim 10, further comprising:
    an alarm system to send an alarm responsive to the plausibility check confirming that the detected relative change in position was correct.

12. A status detecting device, which is for attaching to a living being, including a person, comprising:
    a modular unit, including:
        a detecting arrangement to detect a relative change in position of the body of the living being, wherein the detecting arrangement includes an at least one first sensor and an at least one additional second sensor, which includes a height measuring sensor; and an evaluation arrangement to receive, upon detection of the relative change in the position of the body of the living being, at least (i) a signal indicating a detected relative change in position and (ii) data from the height measuring sensor, and to perform a plausibility check by comparing the detected relative change in position with the data from the height measuring sensor;

wherein the relative change in position of the body is detected by the at least one first sensor if the position of the body changes from a first state to a second state.

13. The status detecting device of claim 12, wherein the at least one first sensor includes at least one of an acceleration sensor and a gyroscopic sensor.

14. The status detecting device of claim 12, wherein responsive to the data from the height measuring sensor indicating no relative change in position of the body, the plausibility check indicating that the detected relative change in position was an error, and wherein responsive to the data from the height measuring sensor indicating a relative change in position of the body, the plausibility check confirming that the detected relative change in position was correct.

15. The status detecting device of claim 14, wherein the modular unit further includes an alarm system to send an alarm responsive to the plausibility check confirming that the detected relative change in position was correct.

16. The status detecting device of claim 14, wherein the alarm system is configured to delay the alarm for a predefinable period of time unless the alarm system receives an acknowledgment from the living being indicating that the movement detected by the detecting arrangement was intended.

17. A method for detecting a position of a body of a living being with a status detecting device, the method comprising:
   detecting over a period of time, by a first sensor attached to the body, at least one of an acceleration and angular position of the body;
   determining over the period of time, by an additional sensor, a height position of the body; and
   detecting a relative change in the position of the body of the living being when data from the first sensor indicates that the position of the body has changed over the period of time from a first state to a second state;
   responsive to detection of the relative change in the position of the body, evaluating the detected relative change in the position of the body, by an evaluation arrangement, by performing a plausibility check; and
   responsive to confirmation of the detected relative change in position, sending, by an alarm system, an alarm based on a movement detected by the first sensor,
   wherein the status detecting device includes the first sensor, the additional sensor, and the alarm system,
   wherein the plausibility check compares the detected relative change in position with data for the height position of the body determined over the period of time and confirms the detected relative change in position when the data for the height position of the body indicates a relative change in position of the body.

* * * * *